United States Patent [19]

Glave et al.

[11] 4,199,518
[45] Apr. 22, 1980

[54] 1α,3β-DIHYDROXY-STEROID-5-ENES FROM 1α,2α-EPOXY-STEROID-4,6-DIEN-3-ONES

[75] Inventors: William R. Glave, Chicago; Richard L. Johnson, Melrose Park; Arnold L. Hirsch, Oak Park, all of Ill.

[73] Assignee: Diamond Shamrock Corporation, Dallas, Tex.

[21] Appl. No.: 891,846

[22] Filed: Mar. 30, 1978

[51] Int. Cl.$^2$ ............................................. C07J 9/00
[52] U.S. Cl. ................................................. 260/397.2
[58] Field of Search ..................................... 260/397.2

[56] References Cited

U.S. PATENT DOCUMENTS

| | | | |
|---|---|---|---|
| 3,901,928 | 8/1975 | Hesse et al. | 260/397.2 |
| 3,966,777 | 6/1976 | Mazur et al. | 260/397.2 |

OTHER PUBLICATIONS

Barton, et al., J.A.C.S. 95:8, 2748 (1973).

*Primary Examiner*—Alan L. Rotman
*Assistant Examiner*—Robert C. Whittenbaugh
*Attorney, Agent, or Firm*—Neal T. Levin; Leslie G. Nunn, Jr.

[57] ABSTRACT

Improved yields of 1α,3β-dihydroxy-steroid-5-enes are obtained by the addition of the alkali metal/liquid ammonia reduction products of 1α,2α-epoxy-4,6-dien-3-one steroids to a quenching agent such as liquid ammonia/ammonium chloride mixture. Specific steroids reduced by these procedures include 1α,2α-epoxy-cholesta-4,6-dien-3-one and 25-hydroxy-1α,2α-epoxy-cholesta-4,6-dien-3-one.

6 Claims, No Drawings

1α,3β-DIHYDROXY-STEROID-5-ENES FROM 1α,2α-EPOXY-STEROID-4,6-DIEN-3-ONES

BACKGROUND OF THE INVENTION

1. Field of the Invention

This invention relates to reduction of 1α,2α-epoxy-steroid-4,6-dien-3-ones directly to the corresponding 1α,3β-dihydroxy-steroid-5-enes.

2. Description of the Prior Art

1α,3β-Dihydroxy-steroid-5-enes are useful intermediates in the synthesis of 1α-hydroxy vitamin D derivatives.

Barton et al, J.A.C.S. 95:8, 2748 (1973) describe reduction of 1α,2α-epoxycholesta-4,6-dien-3-one with large excesses of each of lithium metal and ammonium chloride in ammonia/tetrahydrofuran at reflux to obtain 1α,3β-dihydroxycholest-5-ene which is a precursor of 1α-hydroxyvitamin $D_3$.

U.S. Pat. No. 3,901,928 — Hesse et al, issued Aug. 26, 1975, describe direct reduction of 1α-hydroxy-and 1α,2α-epoxy-steroid-4,6-dien-3-ones and corresponding 6-substituted steroid-4-en-3-ones, where the 6-substituent is a reductively eliminatable atom or group, to the corresponding 1α,3β-dihydroxy-steroid-5-ene by reaction with an alkali metal/liquid ammonia or alkali metal/liquid amine reducing agent in the presence of a proton source such as ammonium chloride.

These references utilize various modes of addition to bring the reactants together. For example, a solution of the steroid is added in one or more portions to a solution of the alkali metal in liquid ammonia or a liquid amine, with subsequent addition in one or more portions of the proton source.

Alternatively, improved yields and/or greater ease of isolation of the reduced steroid are claimed if the proton source is initially present in the solution of the steroid starting material in liquid ammonia or liquid amine and the reducing agent is then added in portions. However, these procedures produce 6-ene compounds rather than the desired 5-ene compounds.

U.S. Pat. No. 3,966,777 — Mazur et al, issued June 29, 1976, describe adding 1α,2α-epoxycholesta-4,6-dien-3-one dissolved in a suitable solvent at a low temperature (of about −30° C.) to liquid ammonia, then adding ammonium chloride followed by lithium metal. Suitable solvents include ethers, such as tetrahydrofuran. An excess of ammonium chloride is added and is followed by addition of an excess of lithium. The ammonia chloride and lithium metal additions are repeated several times, usually between 4 and 7 times. The principal product is the undesired 1α,3β-dihydroxycholest-6-ene which is obtained in a yield of about 50 percent.

Improved processes for these useful dihydroxy steroid-5-ene intermediates are needed in the synthesis of 1α-hydroxyvitamin D derivatives.

SUMMARY OF THE INVENTION

Improved yields of 1α,3β-dihydroxy-steroid-5-enes are obtained by the addition of the alkali metal/liquid ammonia reduction products of 1α,2α-epoxy-steroid-4,6-dien-3-ones to a liquid ammonia/ammonium chloride quenching mixture.

Steroids such as 1α,2α-epoxycholesta-4,6-dien-3-one and 25-hydroxy-1α,2α-epoxycholesta-4,6-dien-3one may be reduced by this procedure to 1α,3β-dihydroxycholest-5-ene (1α-hydroxycholesterol) and 1α,3β,25-trihydroxycholest-5-ene (1α,25-dihydroxycholesterol).

DESCRIPTION OF THE PREFERRED EMBODIMENTS

This process is useful in the preparation of 1α-hydroxy steroids of the cholestane series which are precursors for 1α-hydroxylated vitamin D derivatives. The process of the present invention permits production of 1α-hydroxycholesterol and 1α,25-dihydroxycholesterol by a novel, therefore unrecognized modification of a prior art process. An advantage of this process is the preparation of purified 1α-hydroxylated steroids in higher yields than obtained by any previously described method.

The term "cholestane series" as used herein encompasses steroids having in the 17-position the $C_8$ chain characteristic of cholestanes, as well as analogous compounds where this chain is unsaturated or is substituted with one or more hydroxy or methyl groups, these being the 17-side chains found in the D vitamins and vitaminD derivatives. Suitable ketone starting materials for the preparation of such 1α-hydroxy steroids of the cholestane series may be represented by the formula

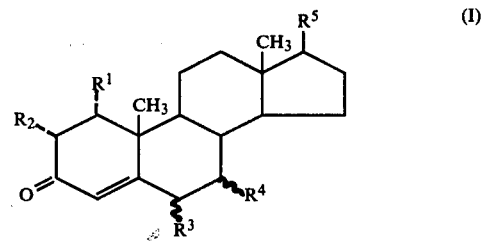

(I)

where $R^1$ is a hydroxyl group and $R^2$ is a hydrogen atom or $R^1$ and $R^2$ together form an epoxide group

and $R^3$ may be hydrogen, hydroxide or a reductively eliminatable atom or group and $R^4$ is a hydrogen atom or $R^3$ and $R^4$ together form a carbon-carbon bond, and $R^5$ is a group

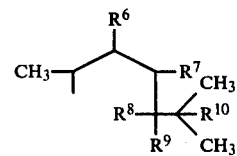

where $R^6$ and $R^7$ each is a hydrogen atom or hydroxyl group or together form a carbon-carbon bond or epoxy group. $R^8$ or $R^{10}$, which may be the same or different, each is a hydrogen atom or a hydroxyl group, and $R^9$ is a hydrogen atom or a methyl or ethyl group.

Reduction of a compound of formula (I) using the process of this invention produces a 1α,3β-diol of the formula

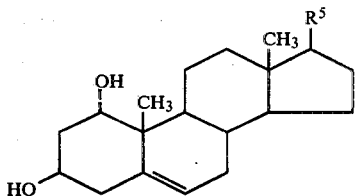

(II)

where $R^5$ is as defined in formula (I).

Alkali metals which may be used in the reducing agent include lithium, sodium and potassium with lithium being the preferred metal. A preferred reducing agent is lithium in liquid ammonia.

Proton sources which may be used in the reduction include ammonium and amine salts, e.g., salts derived from mineral acids, such as the halides, e.g., flouride or chloride, nitrate or sulfate.

The reduction is conveniently carried out in the presence of a solvent, preferably an inert organic solvent such as cyclic ether, e.g., tetrahydrofuran or dioxane or a hydrocarbon solvent such as hexane. It is advantageous to exclude moisture and/or oxygen from the reduction system. When solvent is used, the reduction is conveniently carried out at a temperature between the freezing point of the solvent and 100° C., preferably in the cold.

It is well accepted that vitamin $D_3$ must undergo an obligatory two-step metabolism before its characteristic biological effects, intestinal calcium transport and bone calcium mobilization can be manifested. The ultimate metabolite now recognized as responsible for the known biological effects is $1\alpha,25$-dihydroxyvitamin $D_3$ ($1\alpha,25$-dihydroxycholecalciferol).

Although $1\alpha,25$-dihydroxyvitamin $D_3$ is the most potent and fastest acting form of vitamin $D_3$ known, it has been shown that the administration of $1\alpha$-hydroxyvitamin $D_3$, an analog of vitamin $D_3$, significantly reduces the time required for onset of the intestinal calcium transport and bone calcium mobilization responses, relative to compounds not containing the $1\alpha$-hydroxyl substituent. The use of $1\alpha$-hydroxy-vitamin $D_3$ could circumvent metabolic disorders which prevent the $1\alpha$-hydroxylation from taking place biologically. The obvious therapeutic advantage of using compounds containing the $1\alpha$-hydroxyl moiety made the synthesis of $1\alpha$-hydroxylated compounds a useful endeavor for the organic chemist.

Crystalline $1\alpha,25$-dihydroxyvitamin $D_3$ was synthesized in 8 steps by Barton and coworkers beginning with 25-hydroxycholesterol (J. Chem. Soc. Chem. Comm. 203 (1974)). The latter process described the advantageous, simultaneous introduction of the $1\alpha$-, and $3\beta$-hydroxyl moieties by the lithium/liquid ammonia reduction of 25-hydroxy-$1\alpha,2\alpha$-epoxycholesta-4,6-dien-3-one. The advantage of this process is the predictable stereochemistry of the resulting hydroxyl groups.

In the preferred embodiment described by Hesse, Rizzardo and Barton (U.S. Pat. No. 3,901,928, issued Aug. 26, 1975), the stated yield for the reduction by lithium/liquid ammonia of $1\alpha,2\alpha$-epoxycholesta-4,6-dien-3-one to $1\alpha,3\beta$-dihydroxycholest-5-ene was 39.5% (1.7 g product from 4.3 g starting material). The preferred embodiment described by Hesse et al in Example Ic that afforded the aforementioned yield consisted of the slow addition of a solution of $1\alpha,2\alpha$-epoxycholesta-4,6-dien-3-one (in dry tetrahydrofuran) to a mixture of lithium and ammonium chloride in liquid ammonia containing dry tetrahydrofuran. When the blue color was discharged, steroid addition was discontinued and further lithium and ammonium chloride were added followed by further addition of the steroid solution. This sequence was repeated until all of the steroid was added. At this point, an additional piece of lithium was added followed by additional ammonium chloride.

One modification of this procedure consists of reducing $1\alpha,2\alpha$-epoxycholesta-4,6-dien-3--one in lithium/ammonia prior to protonation of the reaction intermediate enolate with externally added solid ammonium chloride. Our determination that this externally supplied proton source must be added as rapidly as possible led to the present invention. More exactly, when the solid ammonium chloride was added slowly (40-150 minutes) to the reduction reaction mixture, very little of the desired $1\alpha,3\beta$-dihydroxycholest-5-ene could be isolated. When the proton source was added rapidly (less than one minute), the desired product was isolated in high yield. This procedure proved successful for small-scale reactions (5 g or less), but failed completely when attempted on a scaled-up batch (15 g). It was further determined that the addition of the solid ammonium chloride to the larger-scale reaction resulted in uncontrollable foaming, presumably due to heat generation within the reaction flask. As a result, it was necessary to add the solid ammonium chloride to the reduction mixture was slowly (40 to 55 minutes) than had been determined conducive to the production of high yields of the desired reduction product, $1\alpha,3\beta$-dihydroxycholest-5-ene.

It was found in the present invention that the yields of $1\alpha$-hydroxylated steroids derived from the lithium/ammonia reduction of $1\alpha,2\alpha$-epoxy-steroid-4,6-dien-3-ones can be significantly increased by modifying the above procedures. More specifically, the modified reduction with lithium/ammonia of the $1\alpha,2\alpha$-epoxycholesta-4,6-dien-3-one afforded high yields of $1\alpha$-hydroxycholesterol (yields of 54-55% were consistently obtained after purification by direct crystallization). The process employed to obtain these high yields of $1\alpha$-hydroxycholesterol required rapid quenching of the lithium ammonia reduction product by inverse addition of the reaction mixture to a mixture of solid ammonium chloride in refluxing liquid ammonia with or without the presence of tetrahydrofuran. By utilizing the inverse addition procedure described above, it is possible to circumvent the problems associated with slow addition of ammonium chloride to large reaction mixtures. By utilizing the inverse addition procedure, the reduction product is instantaneously protonated upon contact with the ammonium chloride. A unique result of the process of this invention is that it allows the rapid quenching of any lithium ammonia reduction product without regard to the size of the reduction scale-up. Consistently higher yields of $1\alpha,3\beta$-dihydroxycholest-5-ene have been obtained using this process.

For a fuller understanding of the nature of this invention, reference may be made to the following examples which are given merely to illustrate the invention and are not to be construed in a limiting sense. All weights, proportions and percentages are on a weight basis unless otherwise indicated. Likewise, all temperatures are °C. unless otherwise indicated.

EXAMPLE I

This example demonstrates synthesis of 1α-hydroxycholesterol according to the prior art and is outside the scope of this invention.

A 3 liter three-neck round bottom flask was charged with 1000 ml liquid ammonia under a static nitrogen atmosphere. Lithium metal (13.7 g, 1.97 g-atom) was dissolved in the ammonia giving a deep blue/black solution. 1α,2α-Epoxycholesta-4,6-dien-3-one (11.10 g, 0.028 mole) dissolved in 250 ml dry tetrahydrofuran was added dropwise in 30 minutes to the stirred lithium-/ammonia solution. After the steroid was added the mixture was stirred at reflux (−33° C.) for 3 hours. Solid ammonium chloride (70 g) was then added over 40 minutes after which the mixture was stirred an additional hour. Cautious quenching with 20 ml saturated, aqueous ammonium chloride resulted in complete bleaching of the reaction mixture. After standing overnight to evaporate the ammonia, the abundant salts were dissolved in water and the entire mixture extracted with several aliquots of ether. The combined ether extracts were washed with water and evaporated to a small volume. The residue was dissolved in methylene chloride ($CH_2Cl_2$), dried with sodium sulfate ($Na_2SO_4$) and evaporated to give 10.8 g of a brown-orange syrup. TLC (thin layer chromatography) of this material indicated little 1α,3β-dihydroxycholesta-5-ene (1α-hydroxycholesterol) present.

EXAMPLE II

This example demonstrates synthesis of 1α-hydroxycholesterol according to this invention and is within the scope of this invention.

A 1 liter three-necked round bottom flask was charged with 400 ml of liquid ammonia under anhydrous conditions. Lithium metal (6.33 g) was added in small pieces to the ammonia resulting in a deep blue-black solution. 1α,2α-Epoxycholesta-4,6-dien-3-one (5.1 g) was dissolved in a 100 ml dry tetrahydrofuran and added dropwise to the stirred lithium/ammonia solution over 30 minutes. The molar ratio of metal to steroid was 70:1. The dry ice/acetone bath was removed and the mixture refluxed (−33° C.) for 2.25 hours. A quenching mixture was prepared in a second vessel and contained 200 ml liquid ammonia and 15 g solid ammonium chloride. Transfer of the reaction mixture (alkali metal/liquid ammonia reduction products of the steroid) to the quenching mixture through a Teflon ® tube was accomplished with positive nitrogen pressure. An immediate bleaching occurred as the two liquids came in contact. Additional solid ammonium chloride (65 g total) was added when the blue color persisted. After completing transfer, ammonia was allowed to evaporate and the salts dissolved in 100 ml water. The layers were separated and the water layer extracted with ether. The combined organic layers were washed with water until neutral, filtered through anhydrous sodium sulfate and concentrated to dryness. An amber solid (6.1 g) which was 85–90% pure by TLC was crystallized from ethanol to obtain 2.83 g white crystals (54.6% yield) 1α-hydroxycholesterol.

EXAMPLE III

This example demonstrates synthesis of 1α,25-dihydroxycholesterol according to the prior art and is outside the scope of this invention.

110 ml dry ammonia was condensed into an appropriate receiver under anhydrous conditions. A total of 1.7 g lithium metal was added (0.1–0.3 g chunks) to the liquid ammonia at −70° C. to give a deep blue/black solution that was diluted with 70 ml dry tetrahydrofuran. 25-Hydroxy-1α,2α-epoxycholesta-4,6-dien-3-one (1.2 g) was dissolved in 30 ml dry tetrahydrofuran and added dropwise (65 minutes) to the stirred lithium/ammonia solution. The mixture was then stirred at reflux for 3 hours. Solid ammonium chloride (14.1 g) was then added in 750 mg portions at 10 minute intervals to slowly quench the reaction enolate. Product worked up as described above. TLC showed at least 7 to 8 reaction products present of which 1α,25-dihydroxycholesterol represented only ca 5% or less. No pure material was obtained after column chromatography.

EXAMPLE IV

This example demonstrates synthesis of 1α,25-dihydroxycholesterol according to this invention and is within the scope of this invention.

Approximately 100 ml ammonia was condensed into an appropriate reciever under anhydrous conditions. A total of 1.7 g lithium metal was added in small chunks to the ammonia at −70° C. The resulting blue-black solution was stirred at −70° C. for 15 minutes, then diluted with 65 ml dry tetrahydrofuran. 25-Hydroxy-1α,2α-epoxycholesta-4,6-dien-3-one (1.2 g) dissolved in 25 ml dry tetrahydrofuran was added dropwise in 25–30 minutes to the rapidly agitated lithium/ammonia solution. The molar ratio of metal to steroid was 85:1. The addition funnel was washed with an additional 10 ml tetrahydrofuran. After stirring for 15 minutes at −70° C., the reaction mixture was refluxed for 3 hours at liquid ammonia temperature. The entire reaction mixture was quenched by forcing it through a 2 mm Teflon ® tube into a receiving flask containing a stirred, refluxing mixture of ammonia, tetrahydrofuran and ammonium chloride. Transfer was affected by positive nitrogen pressure. The crude reaction mixture contains ca 50% desired product by TLC. After work-up, the golden yellow foam was chromatographed over silica gel (benzene/ethyl acetate). 1α,25-Dihydroxycholesterol (melts 171°–72° C., solidifies and remelts 177°–78° C.) was eluted from the silica gel in ethyl acetate to obtain 0.180 g (14.8% yield).

While the invention has been described with reference to certain specific embodiments thereof, it is understood that it is not to be so limited since alterations and changes may be made therein which are within the full and intended scope of the appended claims.

What is claimed is:

1. A process for the preparation of a compound of the formula

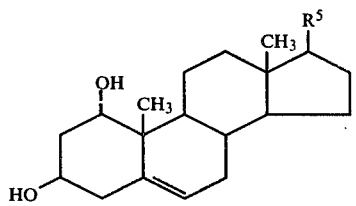

wherein $R^5$ represents a group of the formula wherein R⁶ and R⁷ are each H or OH or together form a carbon-carbon bond or epoxy group, R⁸ and R¹⁰ are each H or OH, and R⁹ is H, CH₃ or C₂H₅, comprising adding the alkali metal/liquid ammonia reduced steroid mixture which has attained thermodynamic equilibrium to a liquid ammonia-ammonium chloride quenching mixture wherein the steroid is a compound of the formula

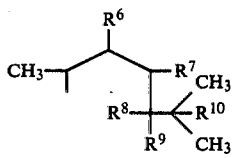

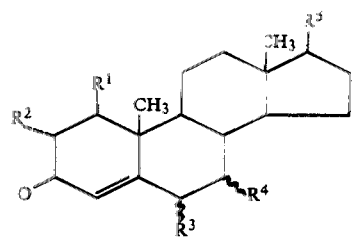

wherein R¹ is OH and R² is H or R¹ and R² together form an epoxide group, R³ represents H, OH or reductively eliminatable atom or group and R⁴ is H or R³ and R⁴ together form a carbon-carbon bond and R⁵ is as defined above.

2. The process of claim 1 wherein the alkali metal is lithium.

3. The process of claim 1 wherein tetrahydrofuran is present in the solution.

4. The process of claim 1 wherein tetrahydrofuran is present in the mixture.

5. The process of claim 1 wherein the steroid is 1α,-2α-epoxycholesta-4,6-dien-3-one and the compound produced from the steroid is 1α-hydroxycholesterol.

6. The process of claim 1 wherein the steroid is 25-hydroxy-1α,2α-epoxycholesta-4,6-dien-3-one and the compound produced from the steroid is 1α,25-dihydroxy-cholesterol.

* * * * *